(12) United States Patent
Jordan et al.

(10) Patent No.: US 6,652,863 B1
(45) Date of Patent: Nov. 25, 2003

(54) METHOD OF REDUCING THE IMMUNOGENICITY OF COMPOUNDS

(75) Inventors: Robert E. Jordan, Malvern, PA (US); Carrie Lynne Wagner, Malvern, PA (US); David M. Knight, Berwyn, PA (US)

(73) Assignee: Centocor, Inc., Malvern, PA (US)

( * ) Notice: Subject to any disclaimer, the term of this patent is extended or adjusted under 35 U.S.C. 154(b) by 0 days.

(21) Appl. No.: 08/433,441

(22) PCT Filed: Nov. 16, 1993

(86) PCT No.: PCT/US93/11148

§ 371 (c)(1),
(2), (4) Date: Jul. 6, 1995

(87) PCT Pub. No.: WO94/11028

PCT Pub. Date: May 26, 1994

Related U.S. Application Data

(63) Continuation-in-part of application No. 07/977,705, filed on Nov. 16, 1992, now abandoned.

(51) Int. Cl.[7] .................. A61K 38/17; A61K 39/395; C07K 14/435; C07K 16/46

(52) U.S. Cl. ................ 424/192.1; 424/133.1; 424/134.1; 424/185.1; 530/387.3

(58) Field of Search .............. 424/133.1, 134.1, 424/185.1, 192.1; 435/69.1, 71.1, 325, 440, 455, 69.6, 70.1, 172.1, 172.2, 172.3, 471; 530/387.3; 536/23.1, 23.4, 23.5, 23.52

(56) References Cited

U.S. PATENT DOCUMENTS

| | | | |
|---|---|---|---|
| 4,816,567 A | 3/1989 | Cabilly et al. ............... 530/387 |
| 4,935,465 A | 6/1990 | Garman ...................... 525/54.1 |
| 5,225,538 A | 7/1993 | Capon et al. ............ 530/387.3 |
| 5,420,264 A | * 5/1995 | Seed et al. | |
| 5,530,101 A | * 6/1996 | Queen et al. | |
| 5,770,198 A | * 6/1998 | Coller et al. | |
| 5,777,085 A | 7/1998 | Co et al. ............... 530/388.23 |

FOREIGN PATENT DOCUMENTS

| | | |
|---|---|---|
| EP | 0 619 324 A1 | 10/1994 |
| WO | WO 89/06690 | 7/1989 |
| WO | WO 89/11538 | 11/1989 |
| WO | WO 91/10722 | 7/1991 |
| WO | WO 93/11161 | 6/1993 |
| WO | WO 93/13133 | 7/1993 |

OTHER PUBLICATIONS

Meredith, et al., "Phase I Trial of Iodine–131–Chimeric B72.3 (Human IgG4) in Metastatic Colorectal Cancer", *J. Nucl. Medicine 33*:23–29 (1992).

Saleh, et al., "Phase I trial of the cimeric anti–GD2 monoclonal antibody ch14.18 in patients with malignant melanoma", *Hum. Antibod. Hybridomas 3*:19–24 (1992).

Osterland, et al., "Anti–γ–Globulin Factors in Human Sera Revealed by Enzymatic Splitting of Anti–Rh Antibodies", *Vox Sang. 8*:133–152 (1963).

Waller, et al., "Immunochemical and Serological Studies of Enzymatically Fragmented Human IgG Globulins–II: Hydrolysis with Subtilisin, Elastase, Trypsin, and Chymotrypsin", *Immunochemistry 6*:207–214 (1969).

Ling, et al., "Antibodies in Human Sera to $F(ab')_2$ Fragments of Monoclonal and Polyclonal IgG", *Int. Archs. Allergy Appl. Immun. 66*:459–463 (1981).

Persselin, et al., "Anti–Fab Antibodies in Humans: Predominance of Minor Immunolglobulin G Subclasses in Rheumatoid Arthritis", *J. Clin. Invest. 76*:723–730 (1985).

Heimer, et al., "The Specificity of Antibodies to the $F(ab')_2$ Fragment of Human IgG", *Arthritis and Rheumatism 28*(5):562–568 (May 1985).

Persselin, et al., "Detection and Significance of Anti–Fab Autoantibody", *Monogr. Allergy 26*:74–81 (1989).

Harris, et al., "Therapeutic antibodies–the coming of age", *TIBTECH 11*:42–44 (1993).

Bhattacharya, et al., "Chimerization of Monoclonal Antibody 7E3 Preserves the GPIIB/IIIA Receptor Blockade and Platelet Functional Inhibition of Murine 7E3", *Clin. Res. 39*:196A (1991).

Capon, et al., "Designing CD4 immunoadhesins for AIDS therapy", *Nature 337*:525–530 (1989).

McCafferty, et al., "Phage antibodies: filamentous phage displaying antibody variable domains", *Nature 348*:552–554 (1990).

Queen, et al., "A humanized antibody that binds to the interleukin 2 receptor", *Proc.Natl.Acad.Sci. USA 86*:10029–10033 (1989).

Ferraiolo, et al., "Goals and Analytical Methodologies for Protein Disposition Studies", In *Protein Pharmacokinetics and Metabolism*, B.L. Ferraiolo et al. (Eds.), Plenum Press, New York, pp. 1–33 (1992).

Jordan, et al., "A Dramatic Reduction of the Immunogenicity of the Anti–GPIIb/IIIa Monoclonal Antibody, 7E3 Fab, by Humanization of the Murine Constant Domains", *Circulation, 83* (Suppl. I): 411, abstract No. 1637 (Oct., 1992).

Kuntz Science 257:1078–1081 (1992).*

Kahan Curr. Opin. Immunol. 4: 553–560 (1992).*

(List continued on next page.)

*Primary Examiner*—Phillip Gambel
(74) *Attorney, Agent, or Firm*—Hamilton, Brook, Smith & Reynolds, P.C.

(57) ABSTRACT

Reduced-immunogenic fusion compounds are disclosed. The fusion compounds of the invention comprise immunogenic compounds linked to auto-antigenic sequences which render the compound less immunogenic. In addition, a method of reducing the immunogenicity of an immunogenic compound is disclosed. The method comprises linking an auto-antigenic sequence to an otherwise immunogenic compound. Recombinant nucleotide sequences encoding auto-antigenic sequences are also disclosed.

30 Claims, No Drawings

OTHER PUBLICATIONS

Tisch et al. PNAS 91: 437–438 (1994).*
Fundamental Immunology Third Edition Raven Press, NY 1993; Ed. W. Paul pp. 1052–1053 only.*
Konrad et al. In Biological Barriers to Protein Delivery Ed. Audus et al. Plenum Press NY 1993 pp. 409–437.*
Knight et al. Mol. Immunol. 32: 1271–1281 (1995).*
LoBuglio, A. F., et al., "Mouse/Human Chimeric Monoclonal Antibody in Man: Kinetics and Immune Response," *Proc. Natl. Acad. Sci. U. S. A.*, 86:4220–4224 (1989).
Coutinho, Antonio, et al., "Natural Autoantibodies," *Current Opinion in Immunology*, 7:812–818 (1995).
Hansen, Morten Bagge, et al., "Influence of Interleukin–6 (IL–6) Autoantibodies on IL–6 Binding to Cellular Receptors," *Eur. J. Immunol.*, 25:348–354 (1995).
Czarnocka, Barbara, et al., "Immunoglobulin Gκ Antithyroid Peroxidase Antibodies in Hashimoto's Thyroiditis: Epitope–Mapping Analysis," *J. Clin. Endocrinol. Metab.*, 82:2639–2644 (1997).
Curtiss, Linda K. and Banka, Carole L., "Selection of Monoclonal Antibodies for Linear Epitopes of an Apolipoprotein Yields Antibodies with Comparable Affinity for Lipid–Free and Lipid Associated Apolipoprotein," *J. Lipid Res.*, 37:884–892 (1996).
Tortorella, Domenico, et al., "Immunochemical Analysis of the Structure of Diphtheria Toxin Shows All Three Domains Undergo Structural Changes at Low pH," *J. Biol. Chem.*, 270(46):27439–27445 (1995).

Gottlieb, Paul D., et al., "The Covalent Structure of a Human γ G–Immunoglobulin. VI. Amino Acid Sequence of the Light Chain," *Biochemistry*, 9(16):3155–3161 (1970).

Edelman, G. M., et al., "The Covalent Structure of an Entire γG Immunoglobulin Molecule," *Biochemistry*, 63(1):78–85 (1969).

Kaku, Seiji, et al., "Comparison of the Antiplatelet Agent Potential of the Whole Molecule, F(ab')$_2$ and Fab Fragments of Humanized Anti–GPIIb/IIIa Monoclonal Antibody in Monkeys," *Gen. Pharmac.* 27(3):435–439 (1996).

Kaku, Seiji, et al., "Antiplatelet and Antithrombotic Effects of YM337, the Fab Fragment of a Humanized Anti GPIIb/IIIa Monoclonal Antibody in Monkeys," *Thrombosis and Haemostasis*, 75(4): 679–684 (1996).

Yano, Shinya, et al., "Natural Antibodies Against the Immunoglobulin F(ab')$_2$ Fragment Cause Elimination of Antigens Recognized by the F(ab')$_2$ from the Circulation," *Eur. J. Immunol.*, 25:3128–3133 (1995).

Wagner, C.L. et al., "Immunological Comparison of Murine and Chimeric 7E3 FAB Fragments in Human Clinical Trials," *Journal of Immunology*, 150(8), Part 2, p. 158A, Abstract No. 895(1993).

* cited by examiner

METHOD OF REDUCING THE IMMUNOGENICITY OF COMPOUNDS

RELATED APPLICATIONS

This application is the U.S. National Phase of PCT/US93/11148, filed on Nov. 16, 1993 and is a continuation-in-part application of U.S. Ser. No. 07/977,705, filed Nov. 16, 1992, now abandoned.

FIELD OF THE INVENTION

The present invention relates to fusion compounds having reduced immunogenicity resulting from the addition to an immunogenic compound of an amino acid sequence that renders the compound less immunogenic. The amino acid sequence is found in human proteins. The present invention relates to a method of reducing the immunogenicity of compounds by the incorporation of an amino acid sequence, the presence of which results in a reduced immune response against the compound.

BACKGROUND OF THE INVENTION

The pharmaceutical use of immunogenic compounds, such as proteins and carbohydrates, for diagnosis or therapy in humans has enormous potential. A major concern, however, is that immunogenic compounds often elicit immune responses which could limit their effectiveness and, in some cases, cause dangerous allergic reactions. This is particularly true of non-human proteins. In addition, it is possible that even proteins with human amino acid sequences could be immunogenic, as in the cases where the protein is altered in structure or conformation as a consequence of manufacturing or where the protein is produced in foreign hosts due to inappropriate post-translational modification or improper folding. Moreover, many non-protein compounds elicit an immune response.

The immune system of the human to whom the immunogenic compound is administered recognizes the compound as "foreign" and mounts an immune response to remove it. The immune response includes the production of specific, high affinity antibodies which bind to and effect elimination of the immunogenic compound.

Monoclonal antibodies (Mabs) provide examples of the therapeutic uses of foreign proteins. Most Mabs are of murine origin, and have generally been found to be immunogenic when injected into humans. Attempts have been made to reduce the immunogenicity of murine Mabs by substituting human constant regions for the analogous murine regions to form chimeric antibodies or chimeric Mabs, or by going one step further and substituting human framework sequences for the murine counterparts in the variable regions of the antibodies (humanized antibodies or humanized Mabs). These approaches may reduce the immune response elicited by murine constant regions or frameworks, but may be ineffective in reducing immune responses directed against the variable regions or idiotypes of the Mabs. Indeed, there are several examples of chimeric Mabs eliciting immune responses directed against the variable regions (for example, B72.3 reported by Meredith, et al., (1992) J. Nucl. Medicine 33:23–29, and ch14.18 reported by Saleh, et al., (1992) Hum. Antibody Hybridoma 3:19–24). In fact, immune responses to the anti-variable region may be the rule rather than the exception. In these cases, another approach is required.

There is a need for therapeutic or diagnostic compounds which do not elicit either an immune response or which elicit a reduced immune response. There is a need for a method of reducing or eliminating the immunogenicity of therapeutic and diagnostic compounds.

The present invention provides reduced-immunogenic compounds which elicit either a reduced immune response or essentially no immune response in humans and a method of reducing the immunogenicity of compounds. Reduced-immunogenic compounds according to the present invention comprise an auto-antigenic amino acid sequence linked to an otherwise immunogenic protein. By associating an auto-antigenic amino acid sequence with an immunogenic protein, the human immune system mounts a reduced immune response against the compound or does not mount an immunogenic response against it all. Accordingly, these compounds can be administered as therapeutics or diagnostics with a reduction or elimination of the problems associated with the administration of immunogenic compounds.

SUMMARY OF THE INVENTION

The present invention relates to reduced-immunogenic fusion compounds which comprise immunogenic compounds linked to auto-antigenic sequences. The presence of the auto-antigenic sequence renders the compound less immunogenic. In addition, the present invention relates to a method of reducing the immunogenicity of an immunogenic compound by linking an auto-antigenic sequence to an otherwise immunogenic compound. The present invention also relates to recombinant nucleotide sequence that encoding auto-antigenic sequences and to essentially pure auto-antigenic peptides.

DETAILED DESCRIPTION OF THE INVENTION

The presence of antibodies in normal human sera which are specific for portions of degraded proteins, such as portions of endogenous proteins degraded by proteolytic enzymes, has been observed. There are many reports in the literature that refer to observed endogenous immunoreactivity to cleaved antibody fragments. This endogenous immunoreactivity to cleaved endogenous proteins is referred to herein as "preimmunity". The antibodies involved in preimmunity immunoreactivity were initially described as "agglutinators" or "anti-Fab antibodies" ("αFABA"). It is reported that preimmunity antibodies 1) are present in most individuals, 2) have varying titers across a population, 3) are not IgM or rheumatoid factors, 4) are fragment specific, and 5) are generally of low affinity. These antibodies can be generally described as a heterogenous group of antibodies that share the characteristic of recognizing endogenous protein fragments, usually the terminal portions of antibody fragments, which are exposed by protein degradation, usually proteolytic degradation.

Osterland, C. K. et al. (1963) Vos Sang 8:133, report a serum activity capable of "agglutinating" Fab- or $F(ab')_2^-$ coated human erythrocytes. The reactivity is directed to epitopes that only become exposed after an immunoglobulin is cleaved by a proteolytic enzyme. That is, these antibodies recognize the degraded protein but not the intact protein.

Waller, M. et al., (1969) Immunochemistry 6:207–214, report that "natural antibodies" in human sera were able to differentiate Fab fragments produced by different enzymes. Different antibodies of this group were specific to different epitopes on Fab fragments which were generated i.e., exposed, by the specific cleavage that a specific Fab fragment underwent.

Ling, N. R. and P. Drysdale, (1981) Int. Archs. Allergy Appl. Immun. 66:459, report that $F(ab')_2$ fragments of human, bovine, and rabbit polyclonal and of human IgG paraproteins of different subclass and light-chain type were coupled to human red cells and used to detect "agglutinator antibodies" in normal and pathological human sera. Such antibodies were reported to commonly occur and demonstrate specificity heterogeneity.

Persselin, J. E. and R. H. Stevens, (1985) J. Clin. Invest. 76:723, report that sera from rheumatoid arthritis patients contained two populations of antibodies directed against the Fab portion of pooled human IgG.

Heimer R., et al., (May 1985) Arthritis and Rheumatism 28(5):562, report an examination of the specificity of IgG anti-F(ab')$_2$ antibodies in unfractionated sera of patients with rheumatoid arthritis and from affinity purified antibody preparations.

Persselin, J. E. and R. H. Stevens (1989) Mongr. Allergy 26:74, report a group of "autologous antibodies" that are directed against the Fab and F(ab')$_2$ portions of human IgG. This group, which was reported to be prevalent in normal individuals and patients suffering a variety of disorders, was characterized to be a heterogenous group of antibodies with diverse biological properties and target specificities.

Although many of the reports of "natural antibodies" relate to the existence of such antibodies that specifically bind to IgG fragments, it is believed that groups these type of antibodies exist which bind to degraded portions of other endogenous proteins.

As used herein, the terms "agglutinators", "agglutinating antibodies", "natural antibodies", "autologous antibodies", "preimmunity antibodies" and "preimmune serum antibodies" are used interchangeably and are meant to refer to antibodies that are normally present in an individual. Preimmunity antibodies are a heterologous group of antibodies which bind to degraded but usually do not bind to intact endogenous proteins. They exist at low levels and generally bind to the terminal portion at a cleavage site of a cleaved endogenous protein. There are some preimmunity antibodies which react to intact proteins. However, many such antibodies recognize fragments but do not bind to the intact protein. In cases in which they do not cross-react with intact proteins, a preimmunity antibody generally recognizes an epitope that occurs at the terminal portion of a protein following cleavage. This epitope usually occurs at the C-terminus. By occurring at these positions, the epitope is extremely specific such that the epitope is only accessible and recognizable when it appears at an end of the protein.

It has been discovered that the presence, on an otherwise immunogenic compound, of an amino acid sequence which forms the epitope for a preimmunity antibody reduces or eliminates the immunogenicity of that compound. The inclusion of such an amino acid sequence allows one to convert an immunogenic compound into a reduced-immunogenic compound.

As used herein, the terms "auto-antigenic sequence", "auto-antigenic peptide", "preimmunity sequence", "preimmunity amino acid sequence" and "preimmunity peptide" are used interchangeably and are meant to refer to an amino acid sequence that is an epitope recognized by preimmunity antibody and that, when associated with an immunogenic compound, renders the immunogenic compound less immunogenic.

As used herein, the terms "fusion compounds", "reduced-immunugenic compound" and "less-immunogenic compounds" are used interchangeably and refer to compounds which comprise an otherwise immunogenic compound linked to an auto-antigenic sequence whereby the presence of the auto-antigenic sequence results in the reduction or elimination of the immunogenicity of the otherwise immunogenic compound. When an immunogenic compound that is a compound that normally elicits an immune response when administered to a patient, is linked with an auto-antigenic sequence to form a fusion compound, the fusion compound elicits no immune response or a reduced immune response when administered to a patient compared to the immune response elicited by the immunogenic compound by itself. The terms "fusion compounds", "reduced-immunogenic compound" and "less-immunogenic compounds" do not encompass c7E3 Fab.

As used herein, the term "less immunogenic" refers to the comparatively reduced-immunogenicity exhibited by an immunogenic compounds linked to an auto-antigenic sequence relative to the immunogenicity exhibited by the same immunogenic compound which is not linked to an auto-antigenic compound.

As used herein, the term "immunogenic" refers to the ability of a compound to elicit an immune response.

As used herein, the term "antigenic" refers to the ability of a compound to react with the immune system, i.e. antibodies.

Auto-antigenic sequences can be identified by a variety methods which can be readily performed by those having ordinary skill in the art. Endogenous proteins, such as antibodies, cytokines, growth factors, receptors, enzymes and structural proteins, can be cleaved by a panel of proteolytic enzymes. The fragments produced can be exposed to human sera and those fragments that bind to preimmunity antibodies in the sera can be readily identified. The amino acid sequence of the epitope that is involved in the preimmunity antibody can be determined. This epitope represents an auto-antigenic sequence. Alternatively, peptide libraries that contain a random assortment of peptides of about 5 or more amino acid residues can be produced. These libraries can be used in a screen with normal human sera to identify peptides that are epitopes recognized by endogenous preimmunity antibodies. These peptides can be identified and used tested as auto-antigenic sequences.

One example of a heterogeneous group of preimmunity antibodies specific for protein degradation products are antibodies which recognize epitopes that occur on the heavy chain C-terminal sequence when IgG antibodies are degraded by proteolytic cleavage. Accordingly, some embodiments of the present invention relate to a method of rendering an otherwise immunogenic compound less-immunogenic by linking to it one of a variety of auto-antigenic sequences found at the heavy chain C-terminus of human or chimeric Fab or $F(ab')_2$ molecules.

Amino acid sequences that are the epitopes for anti-IgG fragment preimmunity antibodies are often found at the hinge region of the heavy chain. Cleavage of the heavy chain at the hinge region generates an amino acid sequence at the C-terminus which may be recognized by specific preimmunity antibodies that do not react with intact IgG molecules. Depending upon where cleavage occurs, a different epitope is exposed and thus a different set of preimmunity antibodies may bind to it. Thus, individual antibodies of this group recognize the discreet epitopes produced by cleavage at various sites.

In some embodiments, the auto-antigenic sequence is derived from the hinge region of IgG. In some preferred embodiments, the auto-antigenic sequences is derived from the hinge region of $IgG_1$.

The hinge region refers to various structural segments of the heavy chain of IgG molecules. Different classes of IgG molecules have different amino acid sequences at their respective hinge regions. The hinge region is a particularly variable element of immunoglobulin structure. Table 1 provides a listing of the different amino acid sequences of the respective hinge regions of the various classes of IgG molecules.

In order to identify whether a particular amino acid sequence is an auto-antigenic sequence, IgG molecules can, for example, be cleaved with one of a panel of proteases to provide IgG fragments that contain different hinge region sequences at the terminal end. Alternatively, peptides and polypeptides can be produced by peptide synthesis or recombinant DNA technology which are modelled upon the sequence of the hinge region. In either case, human sera can be screened to determine whether preimmunity antibodies are present which bind to a particular exposed terminal sequence or synthetic peptide, respectively.

It has been observed that the amino acid sequence near the papain cleavage site of human Fab molecules is reactive with the endogenous human "anti-Fab" preimmunity antibodies. This sequence can instruct the immune system to ignore a molecule that includes it such that no further immune response is elicited. This auto-antigenic sequence prevents an immune response to a linked compound that would be otherwise immunogenic.

A Fab-derived preimmunity sequence having the C-terminal sequence CDKTH (SEQ ID NO:1) was identified from observations made concerning the nature of preexisting human immunity and induced immune responses to murine and chimeric 7E3 Fab fragments. Both the light and heavy chains of the chimeric 7E3 Fab comprises of murine variable regions and human constant regions. This sequence mimics a natural fragment or conformation of human IgG found in human serum, and therefore, a typical high affinity immune response is not mounted against the molecule, or against the related Fab sequence. A reduced immunogenicity of the murine 7E3 variable region when linked to this sequence in the c7E3 molecule was observed. According to the invention, an immunogenic compound, such as a foreign protein, may be rendered non-immunogenic or less immunogenic by linking an auto-antigenic sequence, such as those found at the C-terminus of papain generated human Fab molecules derived from $IgG_1$, to a foreign compound. Thus, association of an auto-antigenic sequence with an immunogenic therapeutic or diagnostic agent is useful for reducing the immunogenicity of the therapeutic or diagnostic agent, thereby preventing or reducing a significant immune response to the agent when administered to a patient. Similarly, papain generated Fab fragments of chimeric antibody c128 which is specific for CD4 and papain generated Fab fragments of chimeric antibody c168 which is specific for tumor necrosis factor have the preimmunity sequence, CDKTH (SEQ ID NO:1), at their the C-termini.

In addition, cleavage of antibodies with human constant regions such as c128, c168 or c7E3 with elastase exposes a preimmunity sequence at the C termini of the antibody fragment thus generated.

The $F(ab')_2$ fragment of chimeric 7E3 has also been found to exhibit a similar characteristic to the Fab molecule, such as showing a natural immunity, or preimmunity, in normal human sera. Therefore, the auto-antigenic sequence at its C-terminal sequence may also be useful for reducing the immunogenicity of foreign compounds in humans.

Preferred auto-antigenic sequences may comprise amino acid sequences selected from the group consisting of: CDKTH (SEQ ID NO:1), PKSCD (SEQ ID NO:2), KSCDK (SEQ ID NO:3), SCDKT (SEQ ID NO:4), DKTHT (SEQ ID NO:5), KTHTC (SEQ ID NO:6), THTCP (SEQ ID NO:7), HTCPP (SEQ ID NO:8), TCPPC (SEQ ID NO:9) and CPPCP (SEQ ID NO:10). These sequences can be associated with the otherwise immunogenic compound in such a way as to ensure that the last residue of each particular sequence represents a C-terminal amino acid residue.

In order to determine whether an amino acid sequence will be useful as an auto-antigenic sequence, peptide constructs comprising the specific sequence to be tested are exposed to human sera to determine whether antibodies are present in the sera which recognize and specifically bind to the sequence.

The most preferred auto-antigenic sequence comprises the amino acid sequence CDKTH (SEQ ID NO:1). As noted above, the H residue is the C-terminal residue of any construction which contains this peptide. When associated with a compound and present at the C-terminal region, this peptide reduces or eliminates the immunogenicity of the compound, thus rendering he compound less-immunogenic.

Once identified, an auto-antigenic sequence can be linked to an immunogenic compound by a variety of means that can be readily practiced by those having ordinary skill in the art. If the immunogenic compound is a protein, a fusion protein comprising the auto-antigenic sequence at the terminal portion of the immunogenic protein can be produced using recombinant DNA technology. A nucleotide sequence that encodes an auto-antigenic sequence can be linked to the nucleotide sequence that encodes the immunogenic protein to form a chimeric gene that encodes a fusion protein. The auto-antigenic sequence will appear at the terminal portion of the resulting fusion protein when the chimeric gene is expressed. If the immunogenic compound is not a protein, synthetic peptides that comprise the auto-antigenic sequence at a terminus can be produced by standard methodology. These peptides can be chemically linked to the immunogenic compound using well known techniques. Auto-antigenic sequences can also be linked to proteins by chemical means. Regardless of the method of linking an auto-antigenic sequence to an otherwise immunogenic compound, the immunogenic compound is converted to a reduced-immunogenic compound by the incorporation of an auto-antigenic sequence which serves as an epitope for preimmunity antibodies. One having ordinary skill in the art can accomplish linkage of an auto-antigenic sequence to an immunogenic compound by well known techniques. Standard coupling techniques, for example, include but are not limited to: coupling through free sulfhydryl of cysteine, coupling through ε-amino group of lysine and coupling through any free amine. Techniques for engineering antibodies are well known and described in Winter and Millstein (1991) Nature 349:293, and Larrich and Fry (1991) Hum. Antibod. and Hybridomas 2:17, both of which are incorporated herein by reference.

According to the invention, an auto-antigenic sequence can be attached to an immunogenic compound in order to convert the immunogenic to a reduced-immunogenic compound. As used herein, the terms "reduced-immunogenic compounds", "less-immunogenic compounds", "non-immunogenic compounds" and "fusion compounds" are used interchangeably and meant to refer to compounds which comprise an auto-antigenic sequence linked to an otherwise immunogenic compound. The presence of the auto-antigenic sequence linked to the otherwise immunogenic compound causes a reduced immune response in individuals administered such compounds relative to the immune response elicited by the immunogenic compound absent the auto-antigenic sequence. An auto-antigenic sequence may be added to non-human proteins, processed or recombinantly produced human proteins or non-protein immunogenic compounds.

Examples of non-human proteins include, but are not limited to, Mabs, Fabs, F(ab')$_2$s, non-human cytokines, non-human growth factors, non-human receptors, non-human structural proteins and non-human enzymes such as Streptokinase.

Examples of processed or recombinantly produced human proteins include, but are not limited to, human and chimeric antibodies and fragments thereof, human cytokines, human growth factors, human receptors, human structural proteins and human enzymes such as coagulation and fibrinolytic agents.

Examples of non-protein immunogenic compounds include, but are not limited to, carbohydrates such as heparin.

A preferred immunogenic compound to be converted to a reduced-immunogenic compound according to the present invention is a murine IgG molecule. Ordinarily, a murine IgG will elicit an immune response when administered to a human. This response can render it ineffective or less effective because the IgG molecule is neutralized and/or removed prior to reaching and binding to its target antigen. By rendering the murine IgG less-immunogenic, it becomes more effective as a therapeutic or diagnostic since it is less deterred by the patient's immune system.

A preferred embodiment of the present invention is a murine IgG molecule having an auto-antigenic sequence comprising CDKTH (SEQ ID NO:1) linked such that the H residue is a C-terminal residue. According to the invention, such a molecule can be produced by standard recombinant DNA techniques used to produce antibodies. For example, a nucleotide sequence encoding the auto-antigenic sequence can be inserted at the 3' end of a gene encoding a C-terminal portion of the IgG molecule, preferably the C-terminal portion of the heavy chain. The nucleotide sequence is inserted in the proper reading frame such that the residues encoded by it will occur at the very end of the resulting protein. The invention, however, does not include the c7E3 Fab.

Clinical results demonstrate a reduction the immunogenicity to foreign antigens containing an auto-antigenic sequence that is exposed by proteolytic cleavage of an IgG heavy chain. Several observations have been made during the development of the therapeutic anti-platelet Mab 7E3 which led to the discovery that the immunogenicity of a normally immunogenic compound may be reduced by associating it with an amino acid sequence which represents an epitope recognized by a preimmunity antibody. These experiments are reported in Example 1.

Briefly, Mab 7E3 was injected into humans both as a murine Fab fragment and as a chimeric Fab fragment (c7E3). The immunogenicity of both fragments were analyzed. There was a fundamental difference in the nature of the immune responses elicited by the murine and chimeric Fabs. The murine 7E3 Fab elicited an immune response in patients which was directed almost entirely against the 7E3 variable region. In contrast, even though the c7E3 Fab contained the identical variable region as murine 7E3 Fab, c7E3 did not elicit comparable immune responses, indicating that the human constant region of the c7E3 Fab rendered the variable region less immunogenic.

Direct-coated, affinity-independent EIA analyses indicated that 50–80% of the normal human population has preimmune serum antibodies that react with chimeric Fab fragments. This preimmunity reactivity is not specific for the variable regions of these molecules since various monoclonal chimeric Fab fragments as well as bulk Fab fragments prepared from total human serum Ig were recognized by the endogenous anti-Fab antibodies. This anti-fragment reactivity appeared to be of low affinity, and was detectable only by relatively sensitive, solid phase EIA assays.

The location of the reactive epitopes of the monoclonal chimeric (or human) Fabs was at the C-terminus of the heavy chain of the Fab fragment generated by papain digestion of the intact IgG molecule. These endogenous anti-chimeric 7E3 Fab preimmunity antibodies were readily neutralized using the Fab fragment of another IgG$_1$ chimeric antibody but not by other proteins. These observations indicated that the reactive epitope is probably a short sequence of amino acids which must be present at or near the C-terminus of the Fab fragment.

A human or chimeric Fab fragment mimics a molecule which is normally found Iin serum and which elicits a normal low affinity antibody response. It appears that the immune response against molecules that contain the auto-antigenic sequence as an accessible epitope may be regulated to preclude a high affinity secondary response. In effect, the immune system may be desensitized or tolerized to antigen challenge with molecules bearing the epitope. Further challenge, therefore, with a similar molecule would not lead to a typical high affinity immune response.

Preimmunity to particular epitopes appears to be species-specific. When the immune responses from primates treated with chimeric 7E3 Fab were analyzed, pretreatment sera from these monkeys demonstrated little or no immunoreactivity to chimeric 7E3 Fab but showed a significant reactivity to Fab fragments generated from monkey IgG. Conversely, human sera showed no preexisting immunoreactivity to monkey Fab. In addition, monkeys have demonstrated a significantly greater induced immunogenicity to chimeric 7E3 Fab than have the humans enrolled Phase I clinical trials.

Other species were also examined for preexisting immunoreactivity to their autologous Fab and F(ab')$_2$ fragments. Autologous panels of sera from rabbits and goats were screened for reactivity to polyclonal Fab and F(ab')$_2$ fragments from IgG of their respective species. Again, it was observed that there as significant IgG reactivity to both of these antibody fragments from their own species. The same observation, however, was not made for murine antibodies to murine 7E3 Fab.

Although comparative experiments on humans have not been performed using murine and chimeric 7E3 F(ab')$_2$ fragments or other murine and chimeric Fab and F(ab')$_2$ fragments, specific antibodies which bind to human Fab and F(ab')$_2$ fragments have been observed. The individuals with high anti-chimeric Fab reactivity do not necessarily have high anti-chimeric F(ab')$_2$ reactivity, and vice versa. Furthermore, the immune recognition of these chimeric fragments is apparently specific, since the binding of anti-Fab antibodies generally cannot be blocked by chimeric Fab' or F(ab')$_2$.

The description of the present invention is generally presented herein as relating to compounds which are non-immunogenic as a result of linking a human auto-antigenic sequence to an otherwise immunogenic compound, and to a method of reducing the immunogenicity of compounds by linking the immunogenic compound with a human auto-antigenic sequence. It is contemplated that the present invention can be applied to other species. The scope of the present invention is intended to include to compounds which are less-immunogenic in a particular species as a result of linking an auto-antigenic sequence form the species to an otherwise immunogenic compound and to a method of reducing the immunogenicity of compounds in a particular species by linking the immunogenic compound with an auto-antigenic sequence from that species.

Furthermore, the description of the present invention is presented as relating to compounds in which an auto-antigenic sequence is physically attached to an otherwise immunogenic compound. However, it is possible that physical linkage is not required. It is contemplated that reduced immunogenicity of a protein can be achieved by co-injection of an auto antigenic peptide sequence or a non-specific human Fab fragments.

EXAMPLES

Example 1

The 7E3 monoclonal antibody has been developed for human therapy as a Fab fragment of the antibody molecule. The reagent was produced in two versions; one derived from the murine monoclonal antibody (murine gamma 1 isotype) by papain digestion (m7E3), and one derived from a mouse/human chimeric monoclonal antibody (human gamma 1 isotype) also by papain digestion (c7E3). The chimeric Mab was produced using standard cloning techniques to obtain the variable region genes from the 7E3 hybridoma and fuse them to previously cloned human constant region genes in vitro. The chimeric genes were introduced into appropriate mammalian cells for expression.

The two Fab molecules have the same variable region, but different constant regions. The C-terminal amino acid sequences exposed after papain digestion are different. Papain clips the antibody molecules in the hinge region of the heavy chain between the CH1 and CH2 domain. The hinge amino acid sequences of the human gamma 1 and the mouse gamma 1 are very different (See Table 1). After cleavage of c7E3 with papain, the C-terminus of the heavy chain ends with the amino acids CDKTH (SEQ ID NO:1). The exact papain cleavage point in the mouse gamma 1 hinge is unknown, but must produce a very different C-terminus from the human sequence, since the mouse hinge does not contain a similar sequence to CDKTH (SEQ ID NO:1).

The m7E3 and c7E3 Fab fragments were tested to determine whether human sera contains antibodies which react with the fragments. A solid phase ELISA assay was used in which either m7E3 Fab or c7E3 Fab was immobilized directly on plastic assay plate and exposed to human serum. Bound human antibodies were detected using goat anti-human antibodies conjugated to an enzyme that will produce a colored product when incubated with the appropriate substrate. This assay is very sensitive and capable of detecting low affinity interactions. A large number of human sera were tested, and the m7E3 Fab was generally non-reactive, whereas c7E3 Fab reacted with at least 60% of the human serum samples.

The specificity of the reactive antibodies in human serum was assessed by including an excess of various molecules in the assay as competitive inhibitors. If a given molecule inhibits binding to c7E3, then it must also display the reactive epitope(s). As expected, soluble c7E3 could inhibit the binding of the human antibodies to immobilized c7E3. Other molecules that could inhibit the binding included Fab fragments of other chimeric gamma 1 antibodies, and polyclonal human Fab derived from serum. In contrast, none of the following molecules could inhibit the binding: 1) m7E3 Fab; 2) whole c7E3 IgG; 3) Fab fragment derived from $IgG_4$ version of 7E3 (contains different hinge region from gamma 1; 4) F(ab')$_2$ fragment of c7E3; and 5) Fab' fragment of c7E3 Fab fragment is extremely specific for the C-terminus exposed after papain digestion of the c7E3 antibody.

The immunogenicities of m7E3 Fab and c7E3 Fab were tested in humans in Phase I clinical trials. Using an assay format that minimizes the low-affinity preimmune reactivity so that actual treatment-related responses can be easily seen, it was found that 17/86 or about 20% of the subjects receiving m7E3 Fab exhibited immune responses at titers ranging from 1:50–1:1600. In contrast, only 1/67 or 1.5% of the subjects receiving c7E3 Fab exhibited an immune response (titer=1:50). The c7E3 Fab, which reacts with endogenous human antibodies, was therefore shown to be must less immunogenic than m7E3 Fab, which does not react with endogenous antibodies.

Example 2

The possible sequences derived from the hinge region of human gamma 1 Fab (and F(ab')$_2$) reactive with endogenous "anti-fragment" preimmunity antibodies can be identified by screening and competition experiments using synthetic peptides. Synthetic peptides of about 5 amino acids or more in length are produced which contain various sequences found in the amino acid sequence of the hinge region.

The most reactive sequences may then be linked to an immunogenic compound of interest to reduce immunogenicity. Linkage can be accomplished in several ways. If the immunogenic compound is a protein, the natural C-terminus of the immunogenic protein can be converted to the desired sequence by site-directed mutagenesis of the gene, most easily accomplished by using appropriately designed PCR primers to delete the natural termination codon and add the desired sequence. These techniques could be used to add or substitute the sequence at any position in any gene. Alternatively, a synthetic peptide can be constructed corresponding to the minimal reactive sequence and could linked to the immunogenic compound by chemical means.

Example 3

Amino acid sequences that are reactive with antibodies in normal human serum, which may be used as auto-antigenic sequences to render foreign or normally immunogenic molecules less-immunogenic, may be identified by screening synthetic peptides with human sera. This is a general method which does not require identification of a protease-specific cleavage site of an endogenous protein, and does not even require that the actual sequence occur naturally.

Briefly, a library of random peptides of at least about 5 or more, and preferably about 5–10 amino acids in length is generated. These peptides are screened for reactivity with antibodies in human sera. This is accomplished, for example, by immobilizing the peptides on a solid phase and performing a standard ELISA assay to detect bound human antibodies after exposure to sera.

Positive peptides are then evaluated further to establish if they are reactive with human sera only and not with other species, and to determine the affinity of the interactions. Peptides that react with the majority of human sera but not sera of other species, are then studied to determine whether they are capable of conferring reduced immunogenicity on otherwise immunogenic compounds. Whether or not a given peptide elicits an immune response requires empirical immunogenicity data.

There are many possible ways to generate and screen libraries or random peptide sequences. One method is to synthesize collections of peptides (Schoofs, P. G. et al. (1988) Immun. 140:611) and assay pools for reactivity against human serum. Positive pools are subdivided and reassayed multiple times so that the active species would eventually be identified. Another method is to generate DNA sequence that codes for random amino acid segments and fuse the DNA sequences to a bacteriophage gene (McCafferty et al., (1990) Nature 348:552). The random amino acid sequences are displayed on the outside of the bacteriophage particle as an artificial C-terminus of a phage protein. The phage is immobilized and screened for reactivity to endogenous human antibodies. Positive phage are isolated and the DNA extracted and sequenced to determine the amino acid sequence of the reactive peptide segment.

Example 4

In general, it is practically difficult to test auto-antigenic sequence candidates in humans to determine whether or not their presence renders immunogenic compounds less immunogenic because it requires experimental testing in humans which raises ethical concerns in many circumstances. Because of this difficulty in testing the immunogenicity of candidate molecules in humans, a rabbit model is used to mimic the human system and demonstrate that epitopes of preimmunity antibodies can be identified and linked to immunogenic compounds to reduce the immunogenicity of the compounds.

Epitopes of preimmunity antibodies can be identified as described in Example 3 but substituting rabbit sera for the human sera used in the protocols described therein. Amino acid sequences that react with the endogenous antibodies can be identified and linked to various compounds by well known methods. Comparative data can be generated from experiments in which the compounds linked to the suspected auto-antigenic sequences and compounds alone are administered to rabbits. The immune response against each of the compounds can be measured.

Rabbits have been shown to exhibit the same type of normal reactivity to homologous Fab fragments; that is, preimmunity to Fab fragments. The appropriate region of rabbit DNA from the immunoglobulin heavy chain locus is cloned and the sequence of the hinge region is determined. This allows the construction of fusion compound which comprise a rabbit auto-antigenic sequence linked to the chimeric 7E3 IgG at the C-terminus of a Fab molecule and evaluating its immunogenicity compared to the immunogenicity of chimeric 7E3 Fab in rabbits.

Example 5

Streptokinase is a thrombolytic protein which has been approved as a drug for heart attack patients suffering coronary blockages. One major disadvantage of Streptokinase is that it is highly immunogenic in humans. Accordingly, its usefulness is greatly limited. Particularly, once a patient has been administered Streptokinase, there is the chance of dangerous immune reaction to any subsequent administration.

The present invention provides a method of reducing the immunogenicity of Streptokinase, thereby reducing the inherent shortcomings of the molecule as a therapeutic which forms the basis for safety concerns that are associated with its use.

Streptokinase production using recombinant DNA technology is well known and can be performed by those having ordinary skill in the art using readily available starting materials. Similarly, well known techniques may be performed to produce a Streptokinase derivative that has the auto-antigenic sequence CDKTH (SEQ ID NO:1) at the C-terminus of the protein. One having ordinary skill in the art can produce such a Streptokinase derivative without undue experimentation.

Streptokinase derivative can be tested in vitro and in animal models to ensure that it retains Streptokinase activity. Comparative clinical experiments can then be performed to measure the immunogenicity of Streptokinase versus the immunogenicity of Streptokinase derivative. The techniques to perform these experiments are well known and can be readily performed by those having ordinary skill in the art.

Example 6

There are several examples of chimeric Mabs which elicit immune responses directed against the variable regions. These include B72.3 (Meredith et al., (1992) J. Nucl. Medicine 33:23–29) and ch14.18 (Saleh, et al., (1992) Hum. Antibody Hybridoma 3:19–24). The fact that these antibodies elicit immune responses represents a major obstacle in their effectiveness and their usefulness is greatly limited by their immunogenicity. Particularly, patients develop antibodies against the antibodies and neutralize their activity.

The present invention provides a method of reducing the immunogenicity of chimeric Mabs, thereby reducing the basis for safety concerns that are associated with its use and increasing their utility. Techniques for engineering antibodies are described in Winter and Millstein (1991) Nature 349:293, and Larrich and Fry (1991) Hum. Antibod. and Hybridomas 2:17. Production of B72.3 and ch14.18 can be accomplished from readily available starting materials using recombinant DNA technology well known by those having ordinary skill in the art. Likewise, well known techniques may be performed to produce chimeric Mab derivatives dB72.3 and dch14.18 in which the auto-antigenic sequence CDKTH (SEQ ID NO:1) is present at the C-terminus of each antibody respectively, preferably the heavy chain. One having ordinary skill in the art can produce such a chimeric Mabs and chimeric Mab derivatives without undue experimentation.

Chimeric Mab derivatives dB72.3 and dch14.18 can be tested in vitro and in animal models to ensure that they retain their specificity and activity. Comparative clinical experiments can then be performed to measure the immunogenicity of chimeric Mabs B72.3 and ch14.18 versus the immunogenicity of chimeric Mab derivatives dB72.3 and dch14.18, respectively. The techniques to perform these experiments are well known and can be readily performed by those having ordinary skill in the art.

TABLE 1

Hinge Sequences of Human and Mouse Immunoglobulins

| Antibody type | Hinge Sequence |
|---|---|
| Human $IgG_1$ | EPKSCDKTHTCPPCP (SEQ ID NO:11) |
| Human $IgG_2$ | ERKCCVECPPCP (SEQ ID NO:12) |
| Human $IgG_3$ | ELKTPLGDTTHTCPRCP (SEQ ID NO:13) |
| Human $IgG_3$M15 | ESKYGPPVPRDCG (SEQ ID NO:14) |
| Human $IgG_4$ | ESKYGPPVPRDCG (SEQ ID NO:15) |
| Mouse $IgG_1$ | VPRDCGCKDCICT (SEQ ID NO:16) |
| Mouse $IgG_{2a}$ | CKPCICTCPPCKCP (SEQ ID NO:17) |

What is claimed:

1. A method of reducing the immunogenicity of an immunogenic compound in a human comprising:
   a) selecting an auto-antigenic sequence from one or more protein fragments and/or peptides that are recognized by human preimmunity antibody,
      wherein said auto-antigenic sequence comprises a carboxy-terminal amino acid sequence that forms an epitope recognized by said human preimmunity antibody; and
   b) linking via a peptide bond said immunogenic compound to the amino-terminus of said auto-antigenic sequence, the carboxy-terminus of said auto-antigenic sequence being unlinked,
      whereby a fusion compound having reduced immunogenicity in a human relative to said immunogenic compound is produced, with the proviso that the fusion compound having reduced immunogenicity in a human is not c7E3 Fab.

2. The method of claim 1 wherein said auto-antigenic sequence is a fragment of an IgG heavy chain constant region amino acid sequence.

3. The method of claim 1 wherein said auto-antigenic sequence is a fragment of an IgG1 heavy chain constant region amino acid sequence.

4. The method of claim 1 wherein the carboxy-terminus of said auto-antigenic sequence consists of an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

5. The method of claim 1 wherein the carboxy-terminus of said auto-antigenic sequence consists of the amino acid sequence of SEQ ID NO:1.

6. The method of claim 5 wherein said immunogenic compound is a protein.

7. The method of claim 5 wherein said immunogenic compound is a non-human protein.

8. The method of claim 5 wherein said immunogenic compound is a variable region of a murine monoclonal antibody.

9. The method of claim 5 wherein said immunogenic compound is Streptokinase.

10. The method of claim 1 wherein said auto-antigenic sequence is linked to said immunogenic compound by chemically binding a peptide comprising said auto-antigenic sequence to said immunogenic compound.

11. The method of claim 1 wherein said immunogenic compound is an immunogenic protein and said linking in step b) comprises expressing a chimeric gene encoding a fusion protein, said chimeric gene comprising a first nucleotide sequence that encodes said immunogenic protein and a second nucleotide sequence that encodes said auto-antigenic sequence, such that expression of said chimeric gene produces a fusion protein having said auto-antigenic sequence linked to said immunogenic protein.

12. The method of claim 1 wherein said auto-antigenic sequence is a fragment of a human protein which has a carboxy-terminus produced by cleavage of the human protein with a proteolytic enzyme.

13. The method of claim 1 wherein said auto-antigenic sequence is derived from the hinge region of a human IgG.

14. A method of reducing the immunogenicity of an immunogenic non-human protein in a human comprising:

a) combining human preimmunity antibody and one or more protein fragments and/or peptides, and selecting an auto-antigenic sequence that is recognized by said human preimmunity antibody from said one or more protein fragments and/or peptides, wherein said auto-antigenic sequence comprises a carboxy-terminal amino acid sequence that forms an epitope recognized by said human preimmunity antibody; and b) linking via a peptide bond said non-human protein to the amino-terminus of said auto-antigenic sequence, the carboxy-terminus of said auto-antigenic sequence being unlinked, whereby a fusion compound having reduced immunogenicity in a human relative to said non-human protein is produced, with the proviso that the fusion compound having reduced immunogenicity in a human is not c7E3 Fab.

15. The method of claim 14 wherein said auto-antigenic sequence is derived from the hinge region of an IgG.

16. The method of claim 14 wherein the carboxy-terminus of said auto-antigenic sequence consists of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

17. The method of claim 14 wherein the carboxy-terminus of said auto-antigenic sequence consists of the amino acid sequence of SEQ ID NO:1.

18. The method of claim 17 wherein said immunogenic non-human protein is a variable region of a murine monoclonal antibody.

19. The method of claim 17 wherein said auto-antigenic sequence is a fragment of a human protein which has a carboxy-terminus produced by cleavage of the human protein with a proteolytic enzyme.

20. The method of claim 1 wherein the carboxy-terminus of said auto-antigenic sequence consists of an amino acid sequence selected from the group consisting of: SEQ ID NO:1, SEQ ID NO:4 and SEQ ID NO:5.

21. The method of claim 14 wherein the carboxy-terminus of said auto-antigenic sequence consists of an amino acid sequence selected from the group consisting of: SEQ ID NO:1, SEQ ID NO:4 and SEQ ID NO:5.

22. A method of reducing the immunogenicity of an immunogenic non-human protein in a human comprising:

a) combining human preimmunity antibody and one or more human IgG fragments that contain hinge region sequences at the terminal end and/or peptides from the hinge region of a human IgG, and selecting an auto-antigenic sequence that is recognized by said human preimmunity antibody from said one or more IgG fragments and/or peptides, wherein said auto-antigenic sequence comprises a carboxy-terminal amino acid sequence that forms an epitope recognized by said human preimmunity antibody; and b) linking via a peptide bond said non-human protein to the amino-terminus of said auto-antigenic sequence, the carboxy-terminus of said auto-antigenic sequence being unlinked, whereby a fusion compound having reduced immunogenicity in a human relative to said non-human protein is produced, with the proviso that said fusion compound having reduced immunogenicity in a human is not c7E3 Fab.

23. The method of claim 22 wherein said human IgG is human IgG1.

24. The method of claim 22 wherein the carboxy-terminus of said auto-antigenic sequence consists of an amino acid sequence selected from the group consisting of: SEQ ID NO:1, SEQ ID NO:4 and SEQ ID NO:5.

25. The method of claim 24 wherein said non-human protein is a variable region of a murine monoclonal antibody.

26. The method of claim 24 wherein said non-human protein is Streptokinase.

27. A method of reducing the immunogenicity of a variable region of a murine monoclonal antibody in a human comprising:

a) combining human preimmunity antibody and one or more human IgG fragments that contain hinge region sequences at the terminal end and/or peptides from the hinge region of a human IgG, and selecting an auto-antigenic sequence that is recognized by said human preimmunity antibody from said one or more IgG fragments and/or peptides, wherein said auto-antigenic sequence comprises a carboxy-terminal amino acid sequence that forms an epitope recognized by said human preimmunity antibody; and b) linking via a peptide bond said variable region to the amino-terminus of said auto-antigenic sequence, the carboxy-terminus of said auto-antigenic sequence being unlinked, whereby a fusion compound having reduced immunogenicity relative to said variable region of a murine monoclonal antibody is produced, with the proviso that said fusion compound having reduced immunogenicity is not c7E3 Fab.

28. The method of claim 27 wherein said human IgG is human IgG1.

29. The method of claim 28 wherein said auto-antigenic sequence consists of an amino acid sequence selected from the group consisting of: SEQ ID NO:1, SEQ ID NO:4 and SEQ ID NO:5.

30. The method of claim 11 wherein said second nucleotide sequence is bound to the 3' terminal end of said first nucleotide sequence.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Cys Asp Lys Thr His
1               5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Pro Lys Ser Cys Asp
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Lys Ser Cys Asp Lys
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Ser Cys Asp Lys Thr
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Asp Lys Thr His Thr
1               5

(2) INFORMATION FOR SEQ ID NO:6:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Lys Thr His Thr Cys
1               5

(2) INFORMATION FOR SEQ ID NO:7:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Thr His Thr Cys Pro
1               5

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

His Thr Cys Pro Pro
1               5

(2) INFORMATION FOR SEQ ID NO:9:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Thr Cys Pro Pro Cys
1               5

(2) INFORMATION FOR SEQ ID NO:10:

(i) SEQUENCE CHARACTERISTICS:
            (A) LENGTH: 5 amino acids
            (B) TYPE: amino acid
            (C) STRANDEDNESS:

(D) TOPOLOGY: linear (ii) MOLECULE TYPE: peptide (xi) SEQUENCE DESCRIPTION: SEQ ID NO:10:

Cys Pro Pro Cys Pro
1               5

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Glu Pro Lys Ser Cys Asp Lys Thr His Thr Cys Pro Pro Cys Pro
1               5                  10                  15

(2) INFORMATION FOR SEQ ID NO:12:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Glu Arg Lys Cys Cys Val Glu Cys Pro Pro Cys Pro
1               5                  10

(2) INFORMATION FOR SEQ ID NO:13:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Glu Leu Lys Thr Pro Leu Gly Asp Thr Thr His Thr Cys Pro Arg Cys
1               5                  10                  15
Pro (2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Glu Pro Lys Ser Cys Asp Thr Pro Pro Pro Cys Pro Arg Cys Pro
1               5                  10                  15

(2) INFORMATION FOR SEQ ID NO:15:

(i) SEQUENCE CHARACTERISTICS:

```
            (A) LENGTH: 13 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Glu Ser Lys Tyr Gly Pro Pro Val Pro Arg Asp Cys Gly
1               5                   10

(2) INFORMATION FOR SEQ ID NO:16:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:16:

Val Pro Arg Asp Cys Gly Cys Lys Pro Cys Ile Cys Thr
1               5                   10

(2) INFORMATION FOR SEQ ID NO:17:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:17:

Glu Pro Arg Gly Pro Thr Ile Lys Pro Cys Pro Pro Cys Lys Cys Pro
1               5                   10                  15
```